US010976292B2

(12) United States Patent
Lindsey et al.

(10) Patent No.: US 10,976,292 B2
(45) Date of Patent: Apr. 13, 2021

(54) SELF-CONTAINED SENSOR MODULE FOR HAZARDOUS LOCATIONS

(71) Applicant: Rosemount Inc.

(72) Inventors: Ryan T. Lindsey, Eden Prairie, MN (US); Glen R. Edwards, Eagan, MN (US); Randon W. Beuc, Prior Lake, MN (US); Michael G. Schwartz, Minneapolis, MN (US)

(73) Assignee: Rosemount Inc., Shakopee, MN (US)

( * ) Notice: Subject to any disclaimer, the term of this patent is extended or adjusted under 35 U.S.C. 154(b) by 81 days.

(21) Appl. No.: 16/143,688

(22) Filed: Sep. 27, 2018

(65) Prior Publication Data

US 2020/0103386 A1 Apr. 2, 2020

(51) Int. Cl.
*G01N 33/00* (2006.01)
*G01D 11/24* (2006.01)
*G01L 19/00* (2006.01)
*G08B 17/117* (2006.01)
*G01F 1/88* (2006.01)
*G01F 23/18* (2006.01)
*G01L 19/06* (2006.01)

(52) U.S. Cl.
CPC ......... *G01N 33/0009* (2013.01); *G01D 11/24* (2013.01); *G01F 1/88* (2013.01); *G01F 23/18* (2013.01); *G01L 19/0046* (2013.01); *G01L 19/0663* (2013.01); *G08B 17/117* (2013.01)

(58) Field of Classification Search
None
See application file for complete search history.

(56) References Cited

U.S. PATENT DOCUMENTS

2007/0102639 A1 5/2007 Cutler et al.
2013/0062223 A1 3/2013 Rabbett

OTHER PUBLICATIONS

International Search Report and Written Opinion for International Patent Application No. PCT/US2019/02641, dated Jan. 10, 2020, date of filing: Sep. 24, 2019, 13 pages.

*Primary Examiner* — Lisa M Caputo
*Assistant Examiner* — Nigel H Plumb
(74) *Attorney, Agent, or Firm* — Christopher R. Christenson; Kelly, Holt & Christenson PLLC (57) ABSTRACT

A sensor module includes a sensor module body, a sensing element within the sensor module body that senses a characteristic of an environment, a breathing element within the sensor module body that allows the sensing element to access the environment, electronics within the sensor module body coupled to the sensing element, and wherein the sensor module body forms a wall of a flame path.

21 Claims, 7 Drawing Sheets

SELF-CONTAINED SENSOR MODULE FOR HAZARDOUS LOCATIONS

BACKGROUND

The process industry often employs gas sensors in order to detect the presence of a particular gas, often as part of a safety system. This is important as many gases may be harmful to human health and/or the environment. Industrial gas sensors are normally mounted near the process area of a plant or control room, or an area to be protected. Generally, industrial gas sensors are installed at fixed locations and to communicate with monitoring systems.

SUMMARY

A sensor module includes a sensor module body, a sensing element within the sensor module body that senses a characteristic of an environment, a breathing element within the sensor module body that allows the sensing element to access the environment, electronics within the sensor module body coupled to the sensing element, and wherein the sensor module body forms a wall of a flame path.

DETAILED DESCRIPTION

Gas detectors are often deployed in industrial environments. These gas detectors may be configured to detect the presence of combustible, toxic, flammable gases, and/or oxygen depletion in the environment. Sometimes these environments can be hazardous. For example, they may contain flammable gases and liquids. This requires the gas detectors to meet certain safety and compliance standards. For example, such detectors may be required to be contained in explosion-proof housings which often include flame paths. This method, particularly designed for systems where there may be an explosive atmosphere due to flammable fluids, is founded on the principle that it is nearly impossible to prevent fluid from penetrating an enclosure, like explosion-proof housings. Therefore, if a flammable fluid penetrates an enclosure, and a trigger is produced, for example, a spark between electrical components, an explosion will occur, but it will remain confined to the enclosure and will not allow the spread of flame to the surrounding environment.

An enclosure must be constructed with the mechanical strength to contain the pressure from an explosion and to allow the controlled escape of explosive gases without igniting the surrounding environment. This is the function of a flame path which is the interface between two parts of an enclosure, for example, the sensor module wall and the sensor housing wall. It allows the gases to exit the enclosure and to cool down during the passage, such that that they are no longer able to trigger an explosion in the surrounding environment. For this reason, flame paths must be sufficiently long and with an interstice narrow enough to cool the gases.

The sensors typically employed within gas detectors degrade over time and need to be maintained or replaced. The sensors should be field-replaceable and should maintain the integrity of the hazardous environment. The demanding standards for hazardous environments make it difficult to service and maintain the sensors, as well as making it more expensive and difficult to manufacture equipment, like sensors and the enclosures that surround them, that can meet the standards.

Current gas sensor systems and designs make service and replacement expensive and difficult for customers. Often, the service and replacement operations themselves can make components of the system susceptible to damage because of the way they are designed. For example, threaded flame path joints may be compromised when accessing the sensor, which in turn compromises the safety of the hazardous environment. Because of the tight tolerances required, removing equipment can be challenging. Flame paths can get, for example, scratched, or otherwise damaged while attempting to remove the equipment, thereby compromising the flame path.

Additionally, current systems and designs often have the breathing element as a separate assembly. This can not only affect the performance of the sensor, but also makes service or removal more time consuming and expensive. The distance between the breathing element and the sensing element directly affects performance. It may affect the accuracy of a reading by not reflecting a true concentration. Additionally, the distance between the breathing element and the sensing element can also affect the response time of the gas detector. In toxic fumes for example, it is desirable to sense them immediately once they occur in a process flow. Having a nonideal distance between the breathing element and the sensing element could cause a delay in sensing the toxic fumes, thereby compromising the safety of the environment. Also, having the breathing element as a separate assembly, requires additional time and cost to remove for repair, and makes the flame paths, for example, more susceptible to damage during service. Further, because the breathing element is part of a separate assembly, it may not be refreshed upon service when the sensing element is removed. Breathing elements may become clogged or worn, for example, and thus they may remain in a faulty state if they are not removed in conjunction with replacement of the sensing element.

Furthermore, the traditional methods for achieving flame path standards for hazardous locations is to use threaded or slip joints. Both methods have drawbacks. Threaded joints require numerous full threads, for compliance with hazardous environment standards, which makes it cumbersome for the customer to service or replace the sensor. It also adds more features to the design which are susceptible to wear and damage. Slip joints require tight fits between the mating parts to maintain control which means the part is more expensive to produce. Additionally, manufacturing and customers can damage the flame path because of the tight fits. Such damage renders the part useless, as it no longer complies with the demanding standards for a hazardous environment.

A gas detector that will reduce the burden and expense associated with sensor maintenance while still complying with the demanding standards for a hazardous environment is needed. One such system, provided herein, includes a self-contained sensor module. The sensor module contains a sensing element, a breathing element, circuit boards, and other electrical components as one piece. By doing this, the sensing element and the breathing element will be characterized together which yields a more accurate measurement. In current designs the breathing element is reused and not unique to the sensing element. Over time the breathing element can become contaminated which reduces the performance of the product. The self-contained module, provided herein, ensures the product will perform to specifications by controlling the distance between the sensing element and the breathing element, which directly impacts the performance, as well as ensuring that the breathing element is replaced when the sensing element is replaced. This design reduces the risk of contamination and ensures that each breathing element is unique to each sensing element.

Furthermore, the self-contained module allows for greater tolerances while still meeting hazardous environment standards. This is achieved by designing the flame path to leverage a multi-step joint. The self-contained module's looser fit between components reduces the chances of the module being damaged either by manufacturing or the customer during installation or service, while still complying with the standards for use in a hazardous environment. Unlike traditional flame path joints, the module is part of the flame path. This ensures that the flame path is renewed when the module is replaced and allows the module cover design to require less thread engagement which reduces the amount of revolutions to open the enclosure, and thus reduces the time needed to remove the cover from the housing.

All of these design features allow for less expensive manufacturing and for less expensive service and replacement, as well as a reduction in the burden on customers, namely, a self-contained sensor module housing all the elements of a sensor and sensor module as one unit, removable and installable in one piece, that comprises a part of a flame path. Additionally, the sensor module can be produced by additive manufacturing. The sensor module can be 3D printed with the breathing element included, which allows the engineers to control the flow of industrial environment fluids to the sensing element in addition to reducing the number of components in the assembly. This design will improve performance by characterizing the breathing element with the sensing element for each sensor module and thus reducing the variance of the breathing element from sensor module to sensor module.

Figure 1:
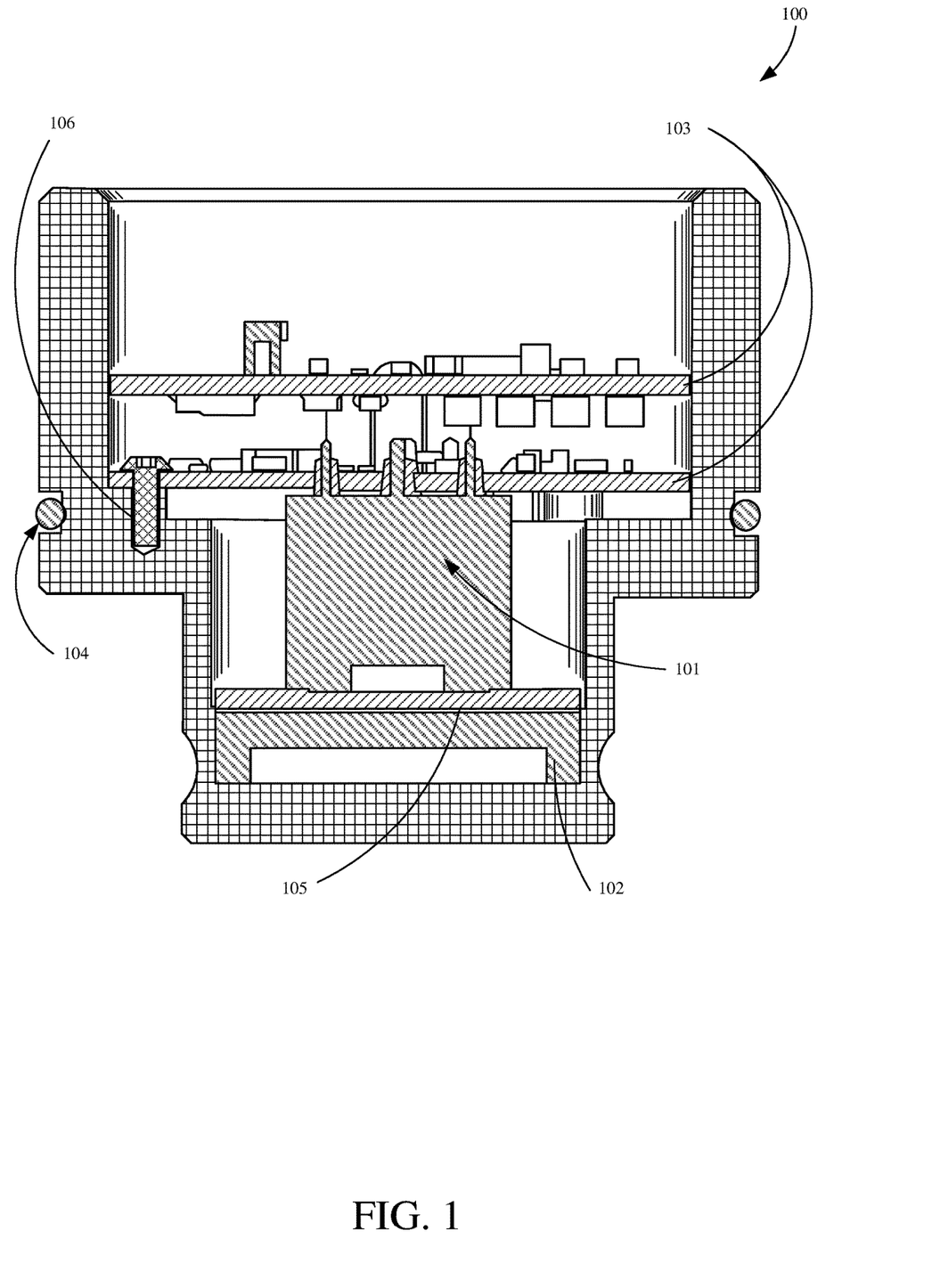
FIG. 1 is a partial cutaway view showing one example of a sensor module.

FIG. 1 is a partial cutaway view showing one example of a sensor module. Sensor module 100 includes sensing element 101, breathing element 102, and electronics 103. Sensor module 100 further includes O-ring 104, gasket 105, and fastener 106. Sensing element 101 can be any number of process analytics sensors used in process environments. Sensor module 100 is scalable such that it may be used with multiple sensing technologies. As a single self-contained unit, sensor module 100 allows for consistent control of the distance between the sensing element 101 and the breathing element 102. The distance directly impacts the performance of the module 100. Breathing element 102 allows sensing element 101 to contact or otherwise be exposed to an ambient environment such that sensing element 101 can sense a gas in the ambient environment. Sensing element 101 and breathing element 102 are preferably separated by gasket 105. Sensing element 101 is electronically coupled to electronics 103. Electronics 103 are coupled to module 100 by fastener 106, here depicted as a screw. It is contemplated that fastener 106 could be any number of various fasteners capable of coupling electronics 103 to sensor module 100.

Electronics 103 can contain any number of components, including, but not limited to, processors, measurement circuitry, communication circuitry, and/or controllers. For example, in one embodiment, sensor module 100 could contain electronics 103 which include measurement circuitry configured to receive a signal from sensing element 101, a processor configured to calculate a sensor-related output, communication logic configured to generate a signal indicative of the sensor-related output, and communicate wirelessly via a transmitter, or through a wired loop, to a display panel, or a user interface (such as a computer in a control room). Electronics 103 could include a controller configured to generate a control signal to have sensor module 100 perform a function based on the sensor-related output or have some other aspect of a process control system perform a function based on the sensor-related output, like the output of an alarm or notification, or the adjustment of a valve, for example.

Sensor module 100 also includes O-ring 104. O-ring 104 is configured to create a seal between sensor module 100 and a sensor module housing (discussed below), preventing the flow of fluids, dust, moisture, and other undesirable materials, between sensor module 100 and a sensor module housing. Sensor module 100 could be made from any number of suitable materials, but particularly those suited for compliance with hazardous location standards. Particularly, but not limited to, non-ferrous metals containing high thermal conductivity like, copper-aluminum alloys, stainless steel, silver, aluminum and galvanized steel, for example, or non-metallic, non-sparking materials like, plastics, woods, and thermoplastic polymers. Such materials are known and commonly used in the manufacture of non-sparking and explosion-proof equipment.

Figure 2:
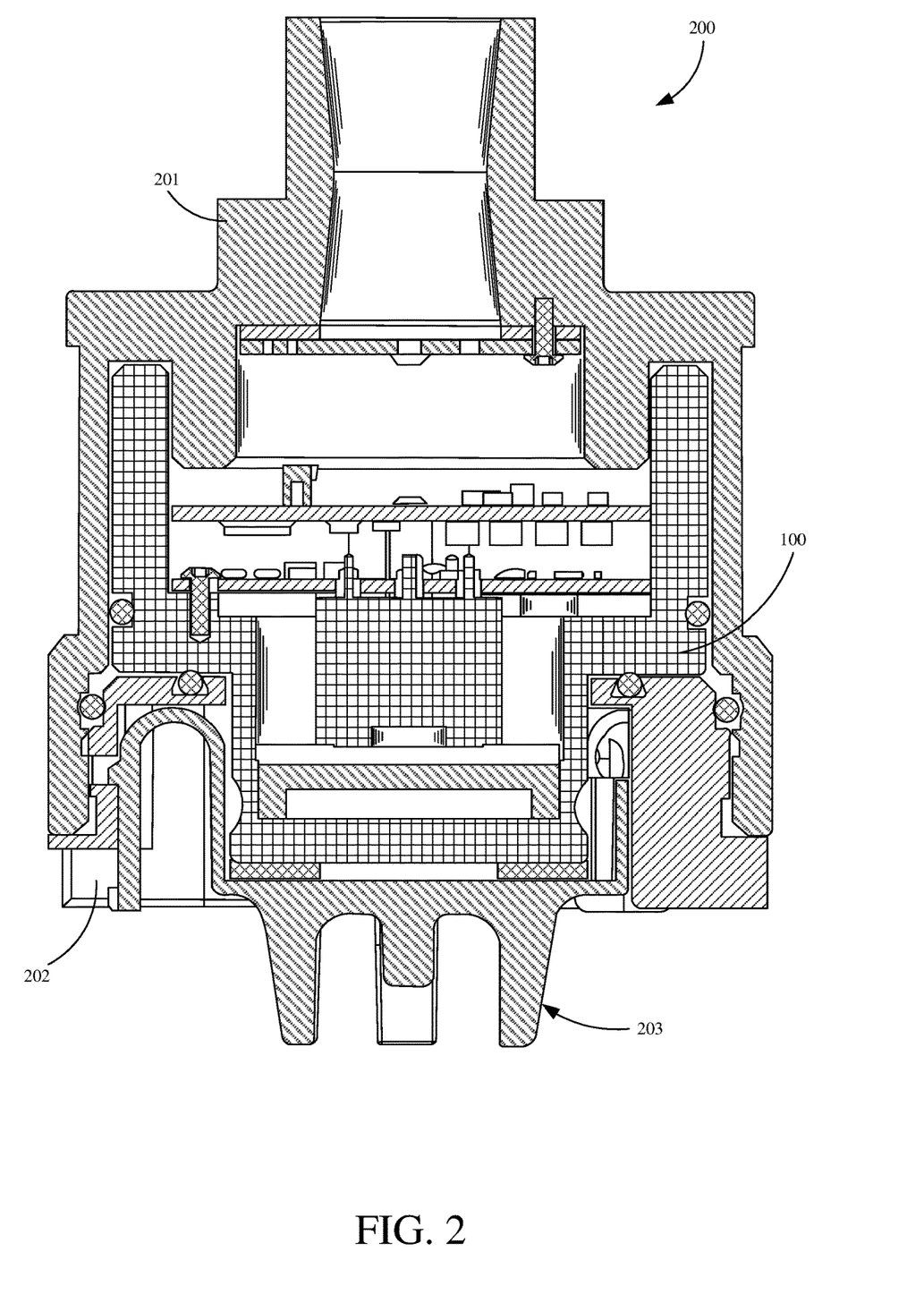
FIG. 2 is a partial cutaway view showing one example of a sensor module installation.

FIG. 2 is a partial cutaway view showing one example of a sensor module installation. Sensor module installation 200 includes sensor module housing 201, sensor module cover 202, ingress protection (IP) filter 203, and sensor module 100. Sensor module cover 202 and sensor module housing 201 fit together over and around sensor module 100, thereby containing sensor module 100 in an explosion proof housing assembly, suitable for use in hazardous environments. While explosion-proof housing is illustratively shown in FIG. 2, it is contemplated that any type of housing could be used. IP filter 203 is typically a hydrophobic filter designed to protect sensors from splashing and spraying liquids and from dust and other debris that may inhibit performance of the sensor.

Sensor module housing 201, sensor module cover 202 and IP filter 203 could be made from any number of suitable materials, but particularly those suited for compliance with hazardous location standards. These materials could include, but are not limited to, non-ferrous metals containing high thermal conductivity like, copper-aluminum alloys, stainless steel, silver, aluminum and galvanized steel, for example, or non-metallic, non-sparking materials like, plastics, thermoplastic polymers, rubber, or any other suitable material.

Figure 3:
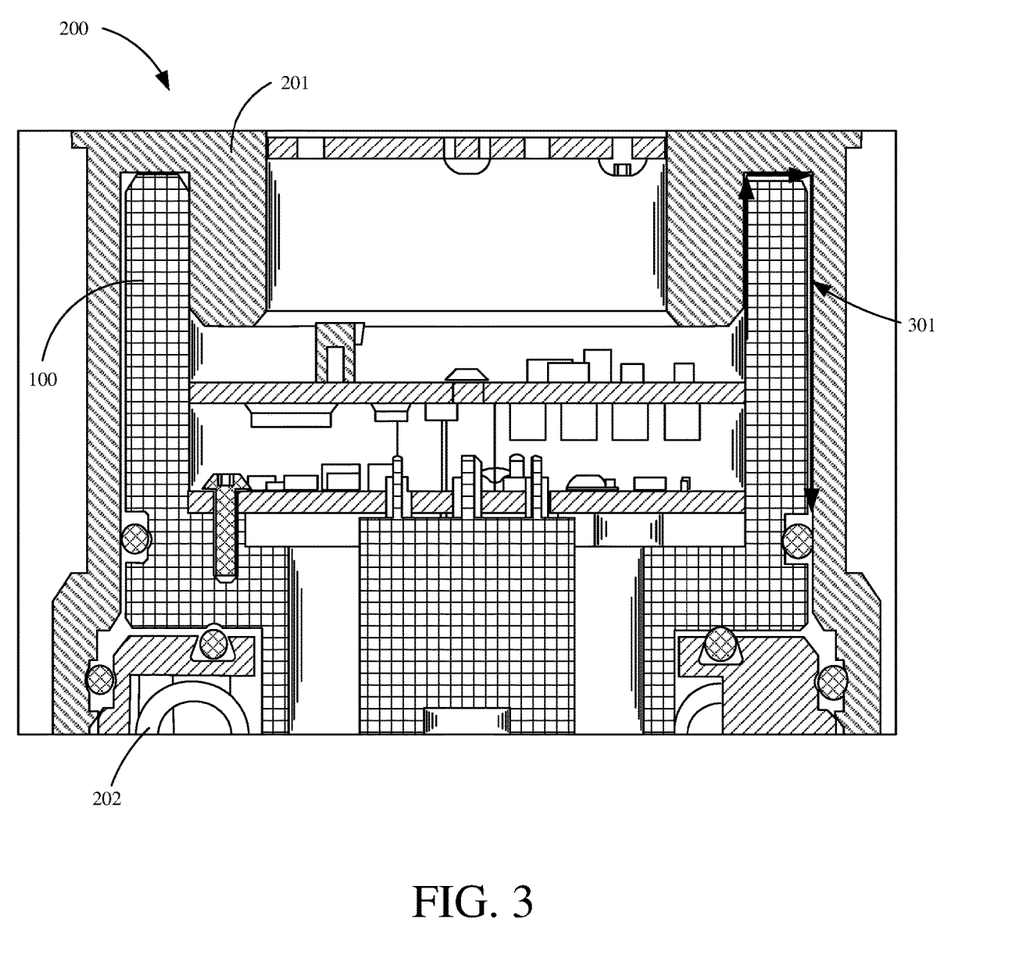
FIG. 3 is a more detailed view of a portion of the sensor module installation showing one example of a sensor module installation including a flame path.

FIG. 3 is a more detailed view of a portion of the sensor module installation showing one example of a sensor module installation including a flame path. Sensor module installation 200 includes sensor module housing 201, sensor module cover 202, sensor module 100, and flame path 301, represented by three arrows. Unlike traditional flame path joints, flame path 301 is formed at least in part by sensor module 100. This ensures that the flame path is refreshed whenever sensor module 100 is replaced, which helps to ensure that the flame path remains effective and in compliance with hazardous environment standards.

As shown in FIG. 3, flame path 301 is a leveraging multi-step joint flame path design formed by the outer wall of sensor module 100 and the inner wall of sensor module housing 201. Multi-step joint flame paths comprise not less than 3 adjacent segments where the path changes direction not less than two times by 90 degrees. The designed segment length, changes of direction and leveraging of flame path 301 allows for reduced tolerances and does not require sensor module 100 to have threads for compliance with hazardous environment standards, because the design can contain the pressure of an explosion and allow gases to cool without threads. With no threading required on sensor module 100, the customer can uninstall sensor module 100 by simply pulling in a direction. The customer can take a new sensor module and install it back into the sensor module installation. The ease of service and removal reduces costs for the customer and reduces the amount of time a customer must be exposed to a hazardous environment during service or replacement operations. Additionally, because this design advantageously allows for reduced tolerances between components within sensor module installation 200, there is reduced risk of damage to installation 200 during service or replacement operations. The reduced tolerances allow for use of less expensive materials during manufacture, particularly the housing 201 and cover 202 because of the nature of the design.

Figure 4:
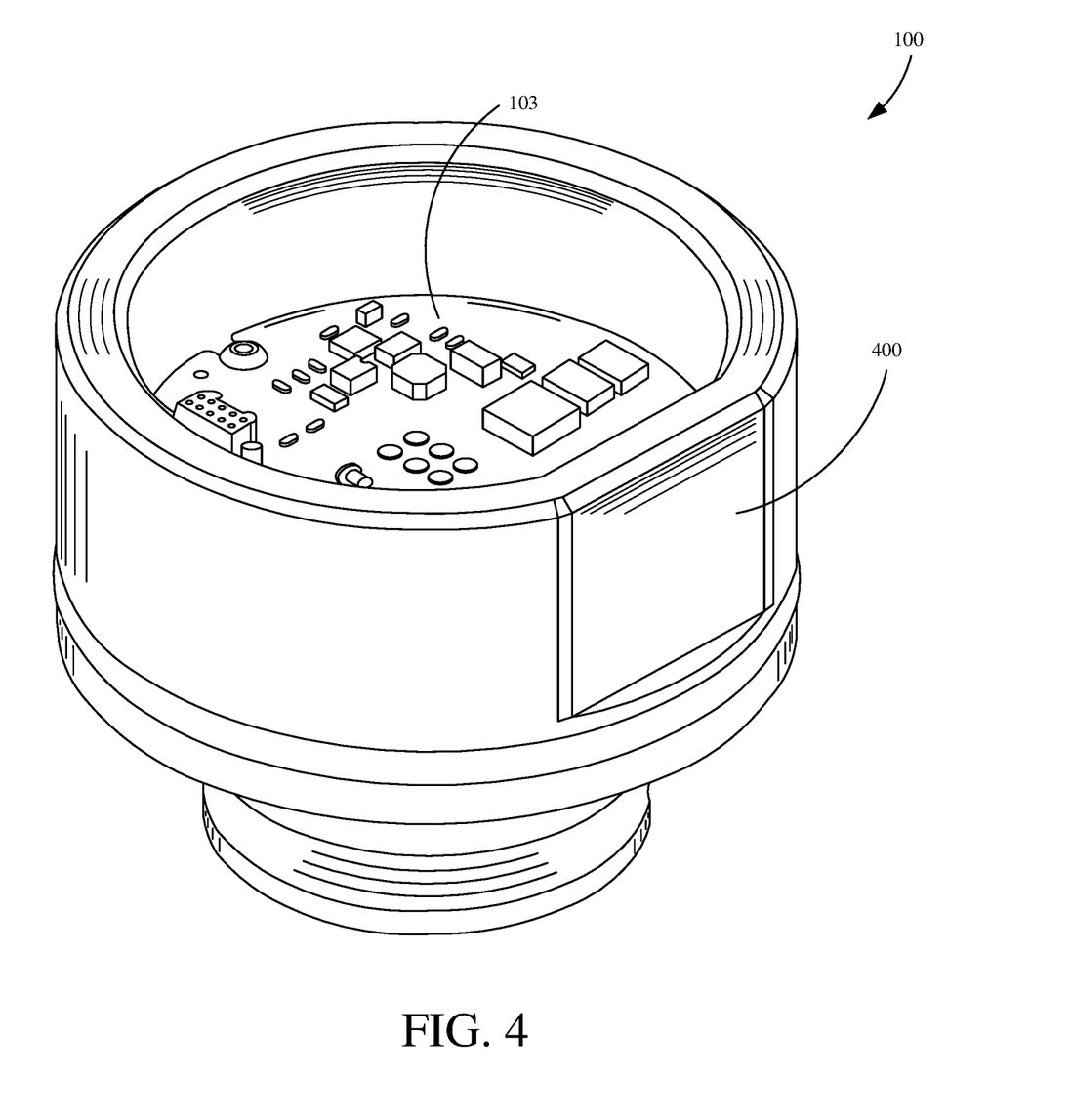
FIG. 4 is a perspective view showing one example of a sensor module including a keying feature.

FIG. 4 is a perspective view showing one example of a sensor module including a keying feature. Sensor module 100 includes electronics 103, and keying feature 400. To ensure the sensor module 100 gets installed correctly in to the housing 201, keying feature 400 is added to the design to allow only one way to install the sensor module 100. Using keying feature 400 ensures that the customer, when installing sensor module 100, has a confirmation that installation was done correctly. Similarly, manufacturing of the sensor module 100 has advantages by using similar keying features to install the electronics in one orientation. The design of sensor module 100 and sensor module installation 200 removes the need for any soldering or potting, thereby reducing costs and increasing efficiency during installation, service and removal.

It is also contemplated that other suitable techniques could be used instead of a keying feature to help the customer guide and confirm the placement of sensor module 100. For example, a design that uses magnets to help guide, align and secure the sensor module could be utilized. The use of magnets would remove the need to have a keying feature on the module which would be less dimensions to control in manufacturing and have approved by approval agencies. Other such features could be tension pins, clips, latching tabs, a plug-in feature, or any other suitable techniques for guiding and securing during installation.

Figure 5:
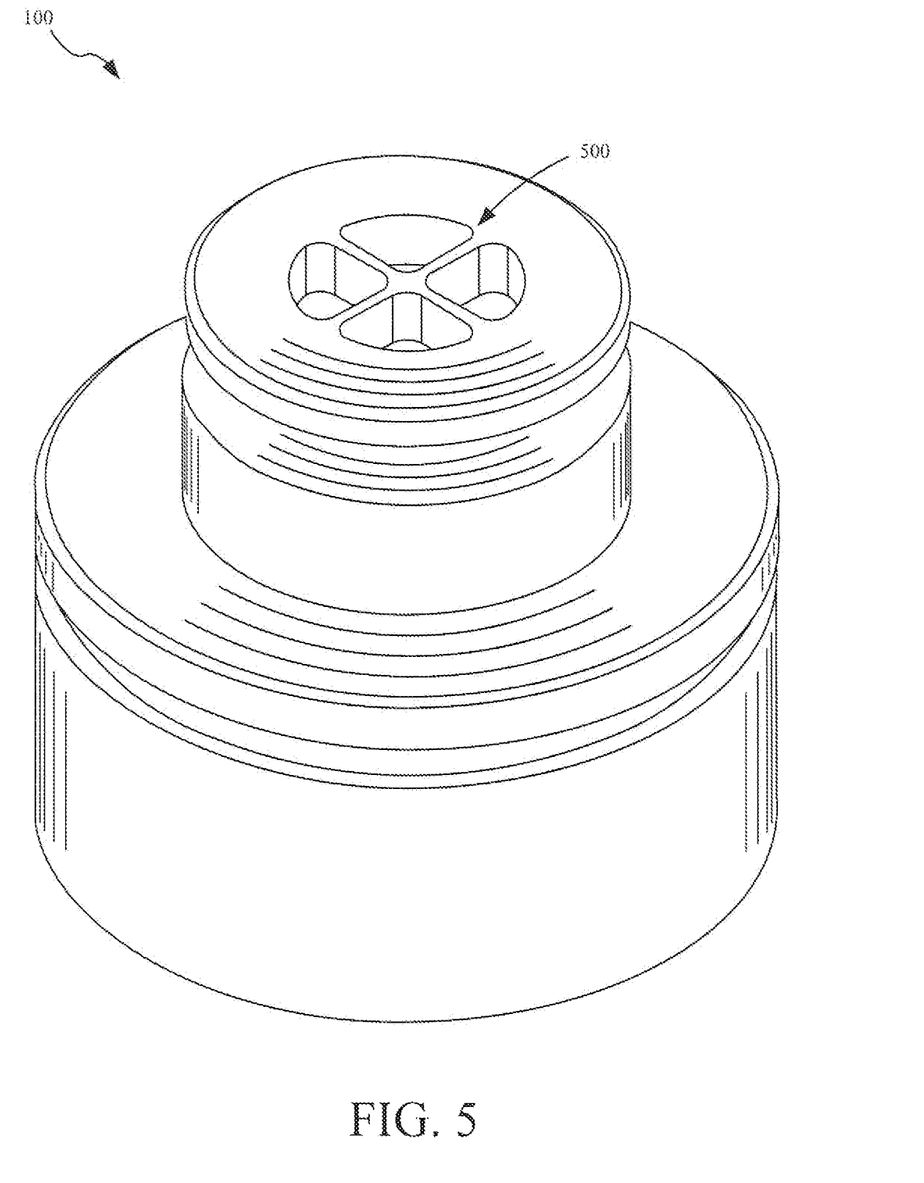
FIG. 5 is a perspective view of the bottom of a sensor module showing one example of a sensor module including an impact guard feature.

FIG. 5 is a perspective view of the bottom of a sensor module showing one example of a sensor module including an impact guard feature. Sensor module 100 includes an impact guard feature 500. Impact guard feature 500 is designed into sensor module 100, as part of the entire whole. Impact guard feature 500 helps to prevent breathing element 102 and sensing element 101 from being damaged. Yet, impact guard feature 500 is perforated thereby allowing sensing element 101 to access and sense characteristics of whatever process flow it is exposed to. Impact guard feature 500 is a part of the sensor module 100, thereby reducing the cost of manufacturing, and ensuring that upon service and removal, impact guard feature 500 is refreshed every time a new sensor module is installed. This design further reducing the susceptibility of buildup on and blockage of impact guard feature 500.

Figure 6A:
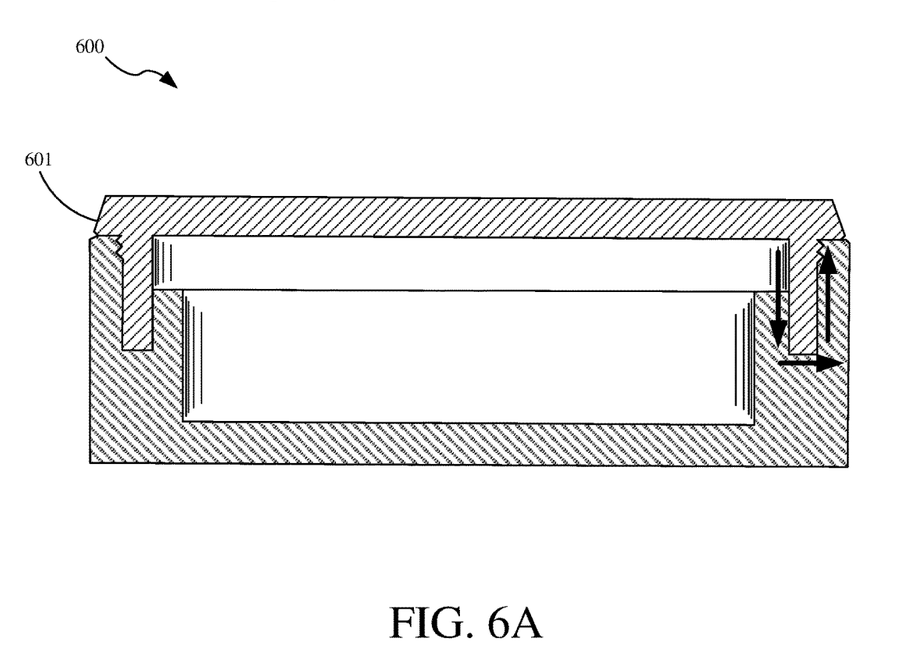
FIG. 6A is a partial cutaway view showing one example of a portion of a sensor module housing and a sensor module cover.

FIG. 6A is a partial cutaway view showing one example of a portion of a sensor module housing and sensor module cover. Sensor module housing and sensor module cover 600 includes cover 601, housing 602, and flame path 603, represented by arrows. The multi-step joint flame path design can be used on a cover 601 that a customer needs to remove to install a device, such as sensor module 100. The designed segment length and changes of direction of the multi-step joint flame path allows for a reduced amount of threads to meet hazardous location standards because the design is able to contain explosive pressure and cool gases with reduced threads. Additionally, the multi-step joint flame path design allows for the use of multi-start threads on the housing 602 and cover 601. Multi-start threads have a greater lead and shallower radial depth requirements than single thread starts and therefore screw and unscrew more quickly. They also require less force to screw and unscrew. However, the greater lead can reduce the holding power because of unequal sharing of the load by each of the individual thread forms and frictional losses while tightening. But when used in combination with a multi-step joint flame path, the potential reduction in holding power is of less concern because the multi-step joint flame path is able to withstand explosive pressure and cool gases while requiring less thread to comply with hazardous environment standards. This design would have many benefits for a customer, such as cost and efficiency. Particularly, the design wouldn't need to have the numerous full threads (sometimes 8 or more) on the cover 601 and housing 602 that is required with other flame path designs, reducing manufacturing costs and the faster screw and unscrew time reduces the amount of time spent in a hazardous location servicing or replacing the sensor module.

Figure 6B:
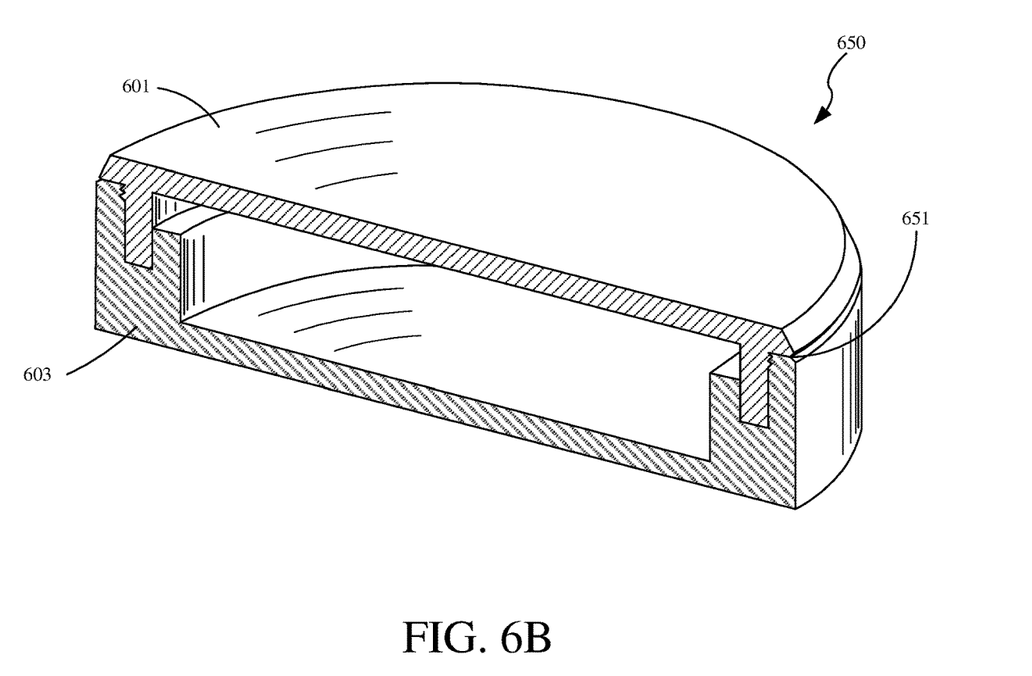
FIG. 6B is a partial cutaway view showing one example of a portion of a sensor module housing and a sensor module cover.

FIG. 6B is a partial cutaway view showing one example of a portion of a sensor module housing and a sensor module cover. Sensor module housing and sensor module cover 650 includes cover 601, housing 602, and threads 651. With this multi-step joint flame path design, the amount of threads needed to meet hazardous location standards can be reduced, thus saving manufacturing cost, and increasing installation and service efficiency thus reducing cost to the customer.

Figure 7:
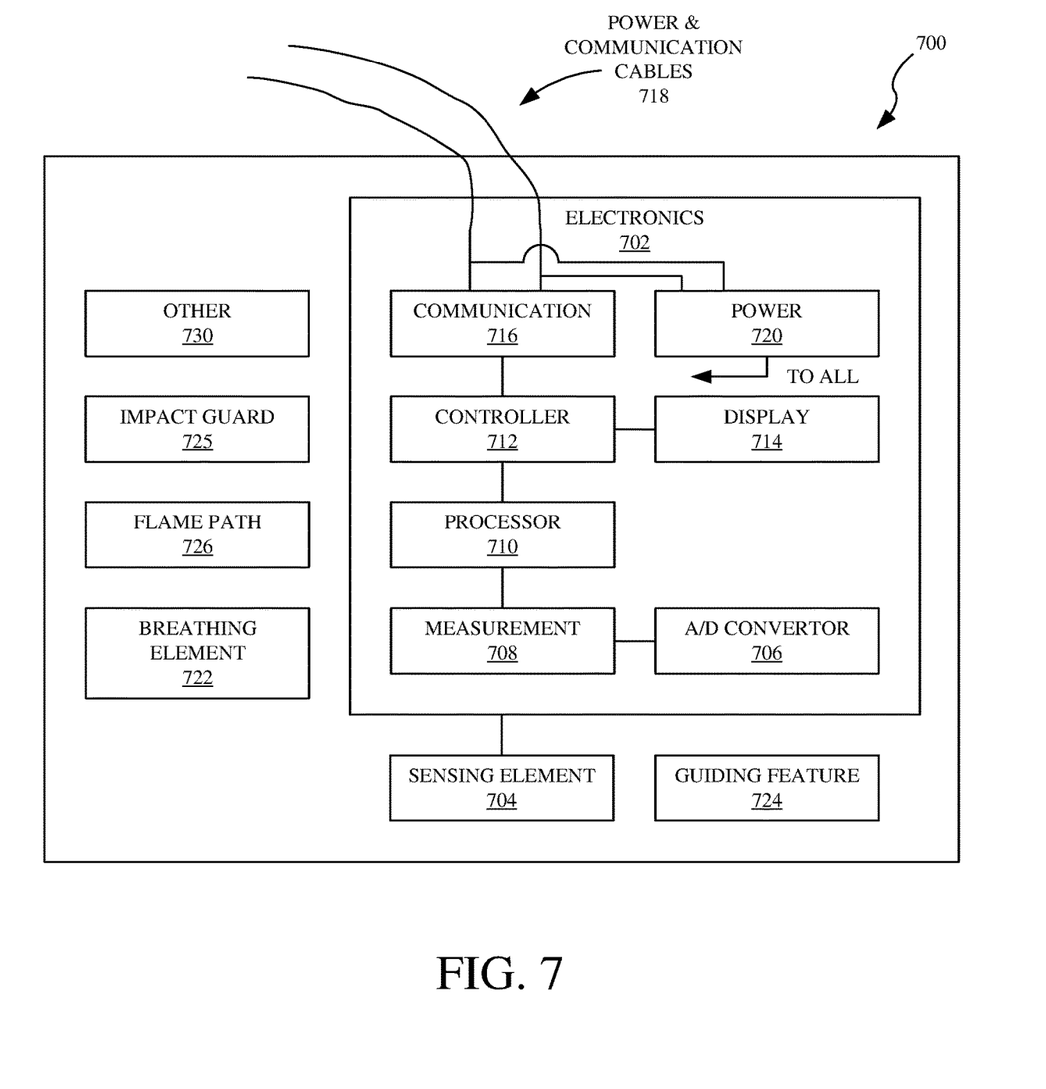
FIG. 7 is a block diagram showing one example of a sensor module.

FIG. 7 is a block diagram showing one example of a sensor module. Sensor module 700 includes, electronics 702, sensing element 704, analog/digital convertor 706, measurement circuitry 708, processor 710, controller 712, display 714, communication circuitry 716, power and communication cables 718, power 720, breathing element 722, guiding feature 724, flame path 726, impact guard 728, and other 730.

Sensing element 704 senses a characteristic of a process flow or environment and generates a sensor signal indicative of the characteristic of the process flow or environment. Electronics 702 are coupled to sensing element 704. Electronics 704 receive the sensor signal from sensing element 704. Analog/digital convertor 706 converts the sensor signal from analog to digital. Measurement circuitry 708 receives the converted signal form convertor 706 and generates a measurement signal, indicative of a characteristic of the process flow, based on the sensor signal. For illustrative example, sensor signal from sensing element 704 could be a raw millivolt signal, which would be converted by convertor 706, and then translated into a signal indicative of a concentration of gas by measurement circuitry 708. Processor 710 receives the measurement signal and generates a sensor-related output based on the measurement signal. Processor 710 could run a number of diagnostics/analytics in generating the sensor-related output. For example, processor 710 could receive a concentration of gas measurement and generate a sensor-related output like a derivative of detected gas concentrations. Processor 710 could further compare the sensor-related output to a pre-set threshold for the purposes of calibration, determining accuracy, determining if an adjustment to the input or output of the process flow is needed, and the like.

Controller 712 receives the sensor-related output from processor 710 and issues a control signal based on the sensor-related output. The control signal could be to display the sensed, measured, and determined data on display 714, or some other user interface such as a computer in a control room. The control signal could also be to generate an alarm or to adjust another element of the process control system through communication circuitry 716. For example, if a gas concentration measurement came in high or low based on the desired threshold, the controller could reduce or increase the input of a component of the process to adjust the concentration of the detected gas in the process environment by, for example, opening or closing a valve. Similarly, if a determination of the derivative and comparison to a threshold suggested that calibration was necessary, an alarm could be generated by controller 712 which could be sent, via communication circuitry 716, to a user interface or to an audible or visible alarm feature.

Communication circuitry 716 receives the control signal from controller 716 and communicates it to a user interface such as a computer in a control room, a remote device, a handheld device, or a display. Communication circuitry could send the signal via power and communication cables 718 or it could communicate wirelessly via a transmitter. Power 720 provides power to the components of electronics 702. Power 720 may be coupled to and draw power from power and communication cables 718, as shown, or power 720 could be a self-supplied power source such as, but not limited to, a battery.

Breathing element 722 is configured to allow sensing element 704 to contact the process flow or sample solution. Breathing element 722 allows for the passage of a fluid from a process flow or a sample solution such that sensing element 704 can sense a characteristic of the process flow or sample solution or an environment. Guiding feature 724 is configured to guide sensor module 700 into a sensor module housing such that a user will know that sensor module 700 is correctly installed into the sensor module housing. Guiding feature 724 could be a keying feature or magnets as described above, or any other sufficient form of a guiding feature to guide sensor module 700 into the sensor module housing such that the user will know that it is correctly installed.

Flame path 726 is configured to create a pathway for flames and fluids to travel in the event of an explosion, the pathway is configured to cool the flames and fluids such that, in the event of an explosion, the risk of igniting the outside environment will be mitigated. The pathway must be sufficiently long and/or change direction enough to effectively cool the flames or fluids when they contact the sides of the pathway. A proper flame path must allow the fluid to enter, pass, and cool down before escaping the enclosure, they are usually long and narrow, and prolong the escape of fluid. In one embodiment, flame path 726 is a multi-step joint flame path, as discussed above, which has numerous advantageous. Flame path 726 could also be any number of sufficient flame paths to meet the standards of a hazardous environment, including, but not limited to: threaded joints like cylindrical joints or tapered joints; non-threaded joints like spigot joints, conical joints, joints with partial cylindrical surfaces, flanged joints, or serrated joints. In one embodiment, the sensor module comprises a part of the flame path, while the sensor module housing comprises another part of the flame path. This ensures that, in a self-contained sensor module, as described above, the flame path will be refreshed whenever the sensor module is replaced.

Impact guard 728 is configured to protect the components of sensor module 700 from damage. Impact guard 728 is part of the body of sensor module 700. It protects the components of sensor module 700 from impact damage that may occur from, for example, a fall or an over pressurization of the sensor module. Impact guard 728 is configured to provide sufficient protection while still allowing sensing element 704 to access the process flow or sample solution. Impact guard 728 could be a perforated design, as discussed above, or any other design sufficient to allow impact guard to protect the components of sensor module 700 while still allowing sensing element 704 to access the process flow or sample solution such that sensing element 704 can sense a characteristic of the process flow or sample solution.

Other 730 is any other feature of sensor module 700 that may be necessary or advantageous. For example, other 730 could be fasteners, like fastener 106, O-rings, like O-ring 104, or gaskets, like gasket 105. Other 730 could a transmitter, a display, such as, but not limited to, and LCD display, and other various electronics.

Although the present invention has been described with reference to preferred embodiments, workers skilled in the art will recognize that changes may be made in form and detail without departing from the spirit and scope of the invention. Moreover, while embodiments of the present invention have generally been described with respect to a gas detector, embodiments are practicable with any process analytic sensor.

What is claimed is:
1. A sensor module comprising:
a sensor module housing;
a sensing element within the sensor module housing that senses a characteristic of an environment;
a breathing element fixedly disposed within the sensor module housing at a controlled distance from the sensing element that allows the sensing element to access the environment;
electronics n the sensor module housing coupled to the sensing element; and
wherein the sensor module housing forms a wall of a flame path.
2. The sensor module of claim 1, wherein the flame path comprises a multi-step joint flame path.
3. The sensor module of claim 1, wherein the sensor module includes a guide that positions the sensor module into a correct installation configuration.
4. The sensor module of claim 3, wherein the guide comprises a keying feature.

5. The sensor module of claim 3, wherein the guide comprises a magnet.

6. The sensor module of claim 1, wherein the sensor module includes an impact guard that protects the sensing element and the breathing element from damage.

7. The sensor module of claim 1, wherein the wall includes the outside surface of the sensor module.

8. The sensor module of claim 1, wherein the sensor module is adapted for engagement with a sensor module housing and wherein a housing wall forms a wall of the flame path.

9. A sensor module comprising:
a sensor module housing;
a sensing element within the sensor module housing that senses a characteristic of an environment and generates a sensor signal indicative of the characteristic;
a breathing element fixedly disposed within the sensor module housing at a controlled distance from the sensing element that allows the sensing element to access the environment; and
electronics within the sensor module housing coupled to the sensing element and configured to receive the sensor signal and generate an output based on the sensor signal.

10. The sensor module of claim 9, wherein the sensor module includes one half of a flame path.

11. The sensor module of claim 10, wherein the flame path is a multi-step joint flame path.

12. The sensor module of claim 10, wherein the sensor module is adapted for engagement with a module housing wherein the module housing includes a portion of the flame path.

13. The sensor module of claim 9, wherein the sensor module includes an impact guard that protects the sensing element and the breathing element from damage.

14. The sensor module of claim 9, wherein the senor module includes a guide that positions the sensor module into a correct installation configuration.

15. The sensor module of claim 14, wherein the guide comprises a keying feature.

16. The sensor module of claim 14, wherein the guide comprises a magnet.

17. An explosion-proof analytic sensor system, the explosion-proof analytic sensor system comprising:
a sensor module comprising:
a sensing element that senses a characteristic of art environment and generates a signal indicative of the characteristic of the environment;
a breathing element disposed at a controlled distance from the sensing element that allows the sensing element to access the environment;
a first wall of a flame path; and
electronics coupled to the sensing element that receive the signal indicative of the characteristic of the environment and generate a sensor-related output based on the signal indicative of the characteristic of the environment;
a sensor module housing configured to house the sensor module and comprising a second wall of the flame path and a multi-start thread; and
a sensor module cover configured to couple to the sensor module housing and comprising a multi-start thread.

18. The explosion-proof analytic sensor system of claim 17, wherein the sensor module includes a guiding feature configured to guide the sensor module into the sensor module housing.

19. The explosion-proof analytic sensor system of claim 17, further comprising a controller configured to receive the sensor-related output and generate a control signal.

20. The explosion-proof analytic sensor system of claim 19, wherein the controller is further configured to generate an alarm signal.

21. The explosion-proof analytic sensor system of claim 17, wherein the sensor module further comprises an impact guard configured to protect the sensing element and the breathing element.

* * * * *